United States Patent
Solar et al.

(10) Patent No.: US 8,221,447 B2
(45) Date of Patent: Jul. 17, 2012

(54) ANEURYSM COIL DELIVERY SYSTEM

(75) Inventors: Ronald J. Solar, San Diego, CA (US); Yoav Shaked, Tzoran (IL); Glen Lieber, Poway, CA (US)

(73) Assignee: ThermopeutiX, Inc., San Diego, CA (US)

( * ) Notice: Subject to any disclaimer, the term of this patent is extended or adjusted under 35 U.S.C. 154(b) by 885 days.

(21) Appl. No.: 11/685,807

(22) Filed: Mar. 14, 2007

(65) Prior Publication Data
US 2007/0219578 A1 Sep. 20, 2007

Related U.S. Application Data

(60) Provisional application No. 60/781,727, filed on Mar. 14, 2006.

(51) Int. Cl.
*A61M 29/00* (2006.01)
(52) U.S. Cl. ........................................ 606/200
(58) Field of Classification Search .................. 606/200; 604/528
See application file for complete search history.

(56) References Cited

U.S. PATENT DOCUMENTS

| | | | | |
|---|---|---|---|---|
| 4,824,435 | A | * | 4/1989 | Giesy et al. .................. 604/500 |
| 5,669,924 | A | | 9/1997 | Shaknovich |
| 5,882,334 | A | * | 3/1999 | Sepetka et al. ............ 604/164.08 |
| 6,352,551 | B1 | * | 3/2002 | Wang ............................ 623/1.11 |
| 6,527,790 | B2 | * | 3/2003 | Chien et al. ..................... 606/194 |
| 6,544,217 | B1 | | 4/2003 | Gulachenski |
| 2003/0055450 | A1 | | 3/2003 | Cheng et al. |
| 2005/0038467 | A1 | | 2/2005 | Hebert et al. |
| 2005/0273021 | A1 | * | 12/2005 | Burgermeister ............... 600/585 |

FOREIGN PATENT DOCUMENTS

| | | |
|---|---|---|
| EP | 1266629 | 12/2002 |
| WO | WO 0245597 | 6/2002 |
| WO | WO 2004/107965 | 3/2004 |

OTHER PUBLICATIONS

Lee R. Guterman, "Treating Wide-Neck Intracranial Aneurysms", Endovascular Today, Jul. 2005, pp. 40-47, Wayne, PA USA.

* cited by examiner

*Primary Examiner* — Gary Jackson
*Assistant Examiner* — Eric Blatt
(74) *Attorney, Agent, or Firm* — Daniel J. Swirsky; AlphaPatent Associates Ltd.

(57) ABSTRACT

Devices and methods for treating an aneurysm include a single unit having an access element and an occlusion element, the access element providing access to the aneurysm for introducing treatment objects such as coils therethrough while the occlusion element blocks the treatment objects from protruding into the vessel. The access element is an elongated element having an access lumen for direct introduction of coils or for introduction of coils via a microcatheter. The occlusion element is a balloon or an elongated element for introduction of blocking objects such as coils therethrough. In embodiments of the present invention, a distal end of the access element is preshaped at an angle to a longitudinal axis of the device, wherein upon introduction of the device into the vessel, the access element is aligned with the longitudinal axis and at placement of the device adjacent the aneurysm, the access element assumes its pre-shaped configuration.

13 Claims, 15 Drawing Sheets

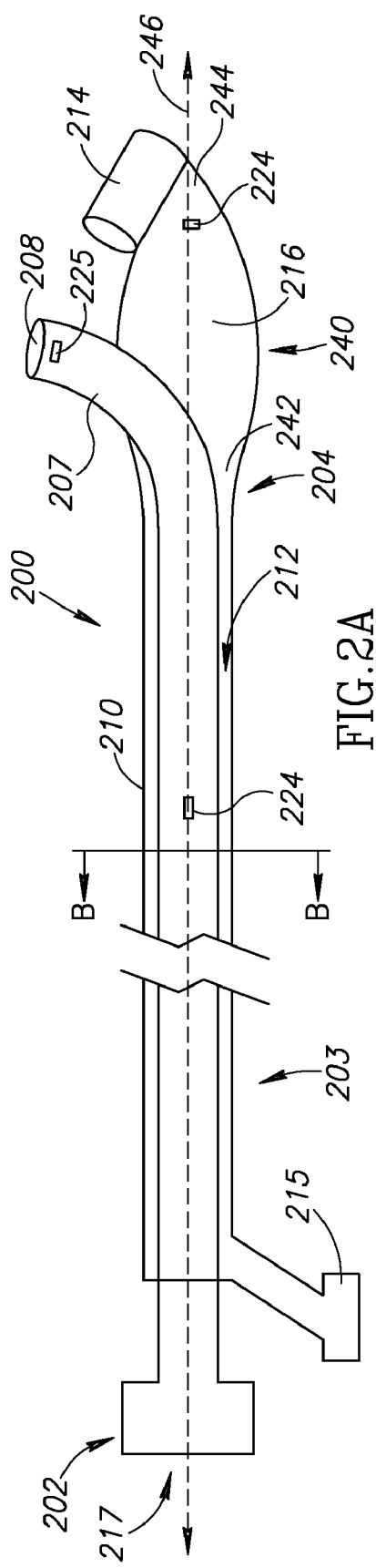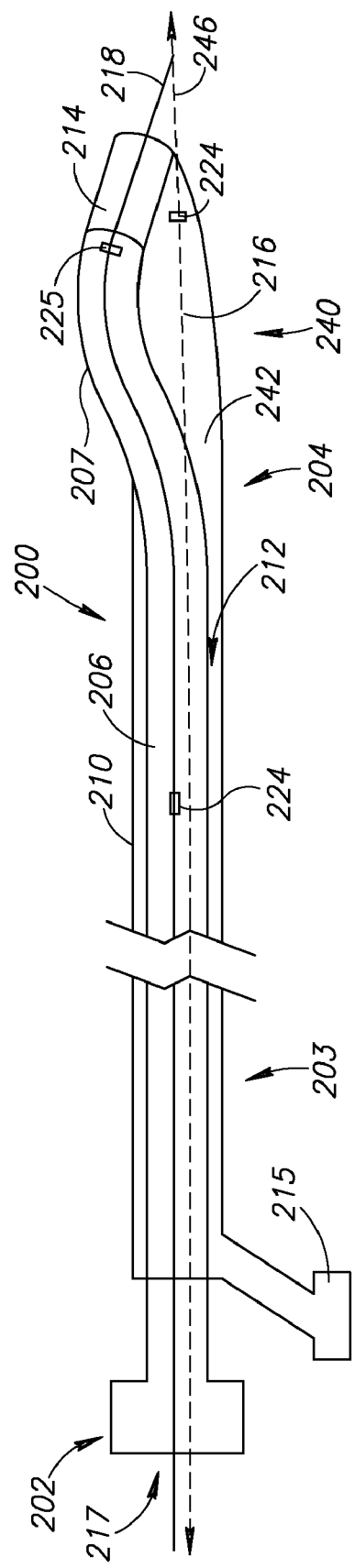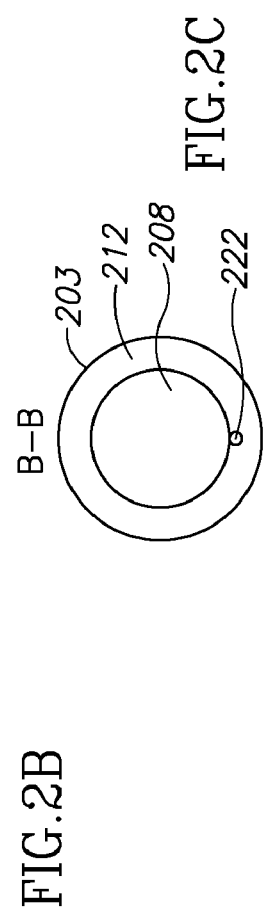

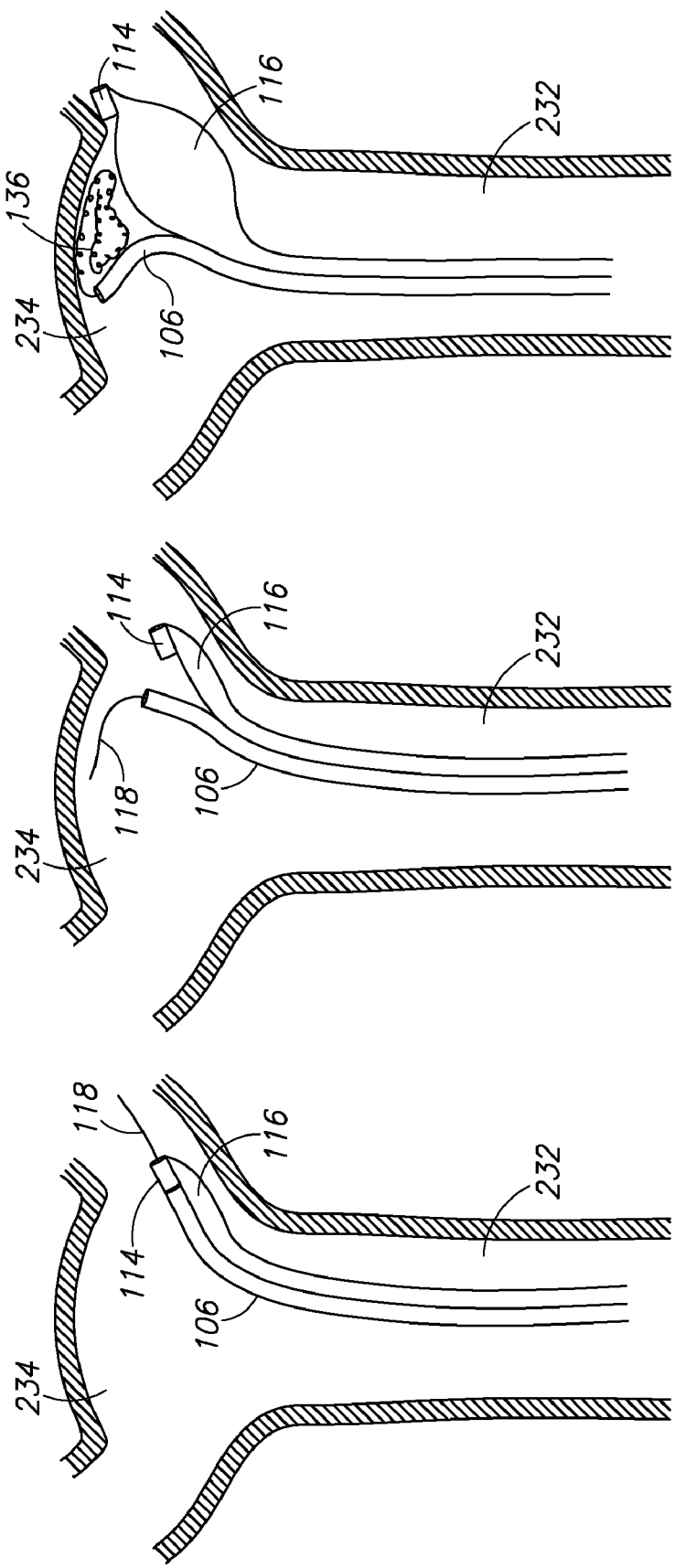

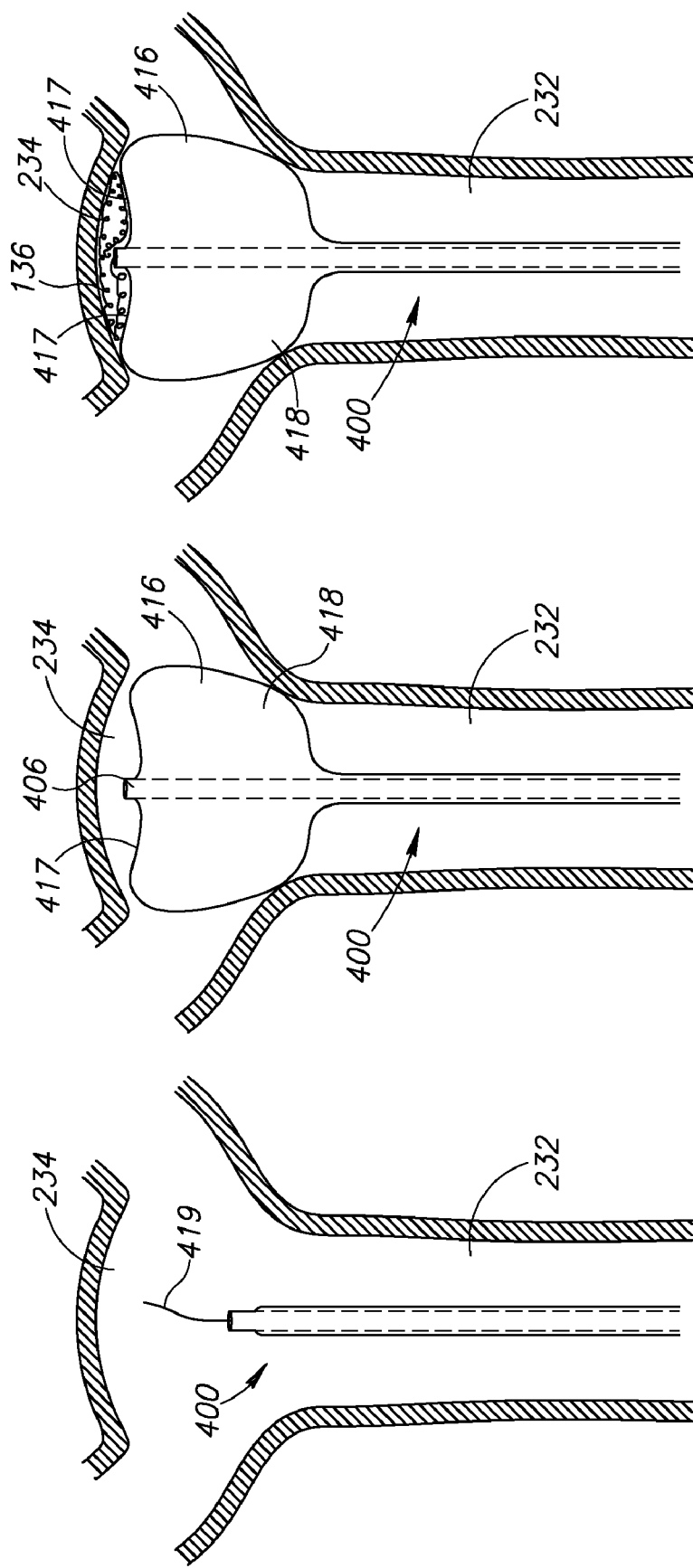

ANEURYSM COIL DELIVERY SYSTEM

CROSS-REFERENCE TO RELATED APPLICATIONS

The present application claims the benefit of U.S. Provisional Application Ser. No. 60/781,727, filed on Mar. 14, 2006.

FIELD AND BACKGROUND OF THE INVENTION

The present invention relates to devices and methods for treating intracranial aneurysms. Treatment of various types of intracranial aneurysms, such as wide-neck and vertebrobasilar aneurysms, has been particularly difficult. Current methods for endovascular treatment for such aneurysms include the introduction of coils into the aneurysm to fill or occlude the aneurysm. However, particularly in cases of wide-neck aneurysm, loops of coils may not be contained within the aneurysm and may protrude out into the vessel. A known technique to prevent escape of the coils is a two-catheter technique, in which a microcatheter and a balloon catheter are introduced simultaneously. For example, in one technique, the microcatheter is placed within the aneurysm, and, during coil delivery, a balloon is inflated in the parent vessel adjacent to the aneurysm orifice. The balloon remains inflated during coil delivery and until the configuration of coils is set, after which the balloon is deflated and the catheter is removed. In another technique, two microcatheters are placed in an aneurysm and multiple coils are introduced.

The use of two devices is cumbersome and can result in wire entanglement, limited pushability and torqueability, increased procedure time and complications.

An alternative method includes the use of self-expanding stents such as, for example, the Neuroform™ stents manufactured by Boston Scientific Corp. (MA, USA). Specifically, such stents are presented to the site of the aneurysm and deployed, and can help to prevent escape of coils. Self expanding stents are generally used due to their low profile and maneuverability, features which are crucial for small vessels associated with intracranial aneurysms. However, they are prone to positioning problems and are difficult to anchor in place during deployment. Furthermore, the use of stents in general is not always considered optimal, since once the stent is in place, it cannot be removed and may itself present additional problems such as turbulence, thrombosis, or even stenosis in the stented region of the vessel. Moreover, the presence of a stent warrants patient-prescribed anti-coagulation medication, which may be contraindicated for some patients.

It would thus be advantageous to have a device which could be used to prevent escape of coils during a procedure which is devoid of the above limitations.

SUMMARY OF THE INVENTION

According to one aspect of the invention, there is provided a device for providing a coil to an aneurysm. The device includes an access element having an access lumen and a distal end which is pre-shaped at an angle to a longitudinal axis of the device and which may be forcibly aligned with the longitudinal axis, and an occlusion element for occluding an ostium of the aneurysm during delivery of the coil, the occlusion element at least partially attached to the access element.

According to another aspect of the invention, there is provided a method for treating an aneurysm. The method includes providing a device having an access element and an occlusion element, the access element having a distal end which includes a pre-shaped configuration which is at an angle to a longitudinal axis of the device, providing a guidewire through the access element and a distal connecting element positioned at a distal end of the occlusion element so as to straighten the pre-shaped distal end, introducing the device into a vessel adjacent to the aneurysm; releasing the guidewire from the distal connecting element so as to cause the access element to assume its pre-shaped configuration, occluding an ostium of the aneurysm the said occlusion element, and delivering a coil through the access element and into the aneurysm.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further advantages of the present invention may be better understood by referring to the following description in conjunction with the accompanying drawings in which:

FIGS. 2A and 2B are schematic illustrations of a device in accordance with further embodiments of the present invention, shown in a deployed state and a pre-deployed state, respectively;

FIG. 2C is a cross-section illustration of the device of FIGS. 2A and 2B, showing an access lumen, an inflation lumen coaxial to the access lumen, and a core wire;

FIGS. 9A-9C are schematic illustrations of the steps of a method of using the devices of the present application to treat an aneurysm at a Y-bifurcation;

FIGS. 10A-10C are schematic illustrations of the steps of a method of using the device of FIGS. 4A and 4B to treat an aneurysm at a Y-bifurcation.

Figure 1A:
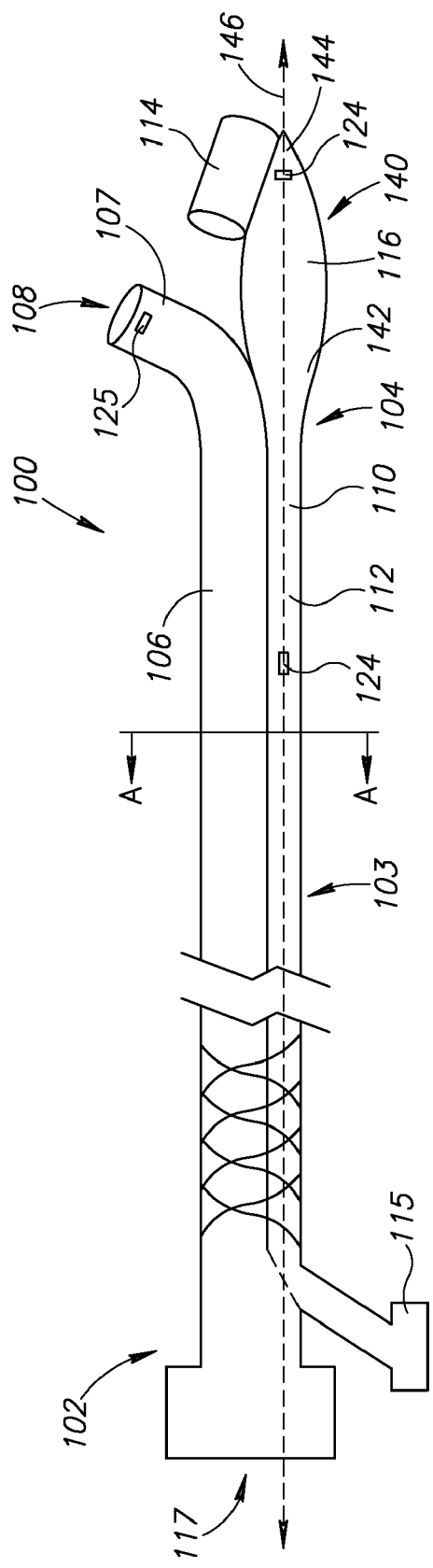
FIGS. 1A and 1B are schematic illustrations of a device in accordance with embodiments of the present invention, shown in a deployed state and a pre-deployed state, respectively.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of the invention. It will be understood by those of ordinary skill in the art that the present invention may be practiced without these specific details. In other instances, well-known methods, procedures, components and structures may not have been described in detail so as not to obscure the present invention.

Figure 1B:
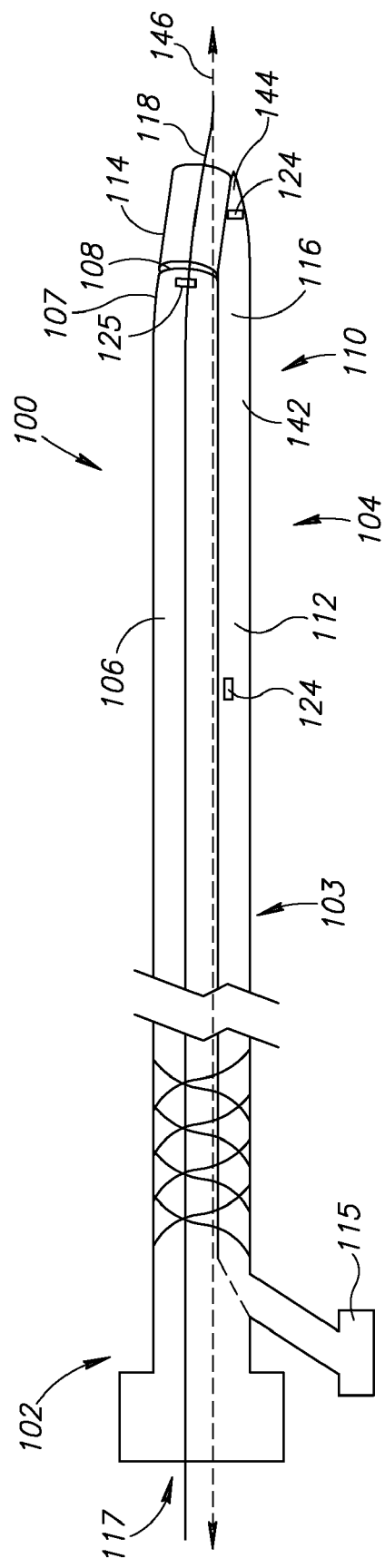

Reference is now made to FIGS. 1A and 1B, which are schematic illustrations of a device 100 in accordance with embodiments of the present invention, shown in a deployed state and in a pre-deployed state, respectively. Device 100 includes a shaft 103 having a proximal end 102 and a distal portion 104. Shaft 103 is comprised of an access element 106 for accessing an area of an aneurysm, and an occlusion element 110, for providing occlusion means to the ostium of the aneurysm. Distal portion 104 of shaft 103 includes an access element distal portion 107 and an occlusion element distal portion 140, wherein occlusion element distal portion 140 includes a balloon 116 having a balloon proximal end 142 and a balloon distal end 144. In the embodiment shown in FIGS. 1A and 1B, access element 106 is an elongated element extending from proximal end 102 of shaft 103 to distal portion 104 of shaft 103, and includes an access lumen 108 therethrough. Proximal end 102 of shaft 103 includes an access hub 117 for introduction of a material or object through access lumen 108. Distal portion 107 of access element 106 extends distally past balloon proximal end 142, and is comprised of a soft elastomeric or polymeric material such as a urethane, silicone rubber, latex, nylon, any copolymers thereof, or any other suitable material. Alternatively, distal portion 107 of access element 106 includes a spring-element that provides pre-shaping. A radiopaque access marker 125 is positioned on distal portion 107 of access element 106. Occlusion element 110 is also an elongated element positioned alongside access element 106 and extending from proximal end 102 of shaft 103 to distal portion 104 of shaft 103. Occlusion element 110 has a balloon 116 at a distal end thereof. Balloon 116 is shown in an inflated state in FIG. 1A and in a deflated state in FIG. 1B. An inflation lumen 112 provides fluid communication between an inflation port 115 at proximal end 102 of shaft 103 and balloon 116. Additional radiopaque markers 124 are positioned along occlusion element 110 and/or shaft 103.

A distal connecting element 114 is positioned at the distal end of device 100, and may be attached to balloon 116. Alternatively, distal connecting element 114 may be attached to a distal tip 119, distal to balloon 116, as shown in FIGS. 1F and 1G, in the inflated and deflated states, respectively. In this embodiment, a radiopaque marker 124 may be positioned on distal connecting element 114. As shown in FIG. 1A, distal portion 107 of access element 106 is pre-shaped at an angle to a longitudinal axis 146 of device 100, wherein longitudinal axis 146 is defined by an imaginary line connecting distal portion 104 and proximal end 102 of shaft 103. The angle can be in a range of 0 to 90 degrees, and in most cases is in a range of 20-70 degrees.

As shown in FIG. 1B, pre-shaped access element 106 can be forcibly aligned with longitudinal axis 146 of device 100 by placing a guidewire 118 therethrough and further positioning guidewire 118 through distal connecting element 114. This relatively straight configuration results in a reduced profile which is suitable for introduction and advancement through blood vessels. In one embodiment, access element 106 acts as a microcatheter for providing treatment coils. In an alternative embodiment, access element 106 acts as a conduit for a separate microcatheter placed therein.

Figure 1C:
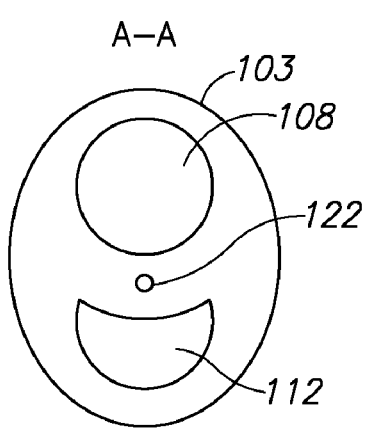
FIGS. 1C, 1D and 1E are cross-sectional illustrations of the device of FIGS. 1A and 1B, showing an access lumen, an inflation lumen and a core wire, in accordance with several configurations.
Figure 1D:
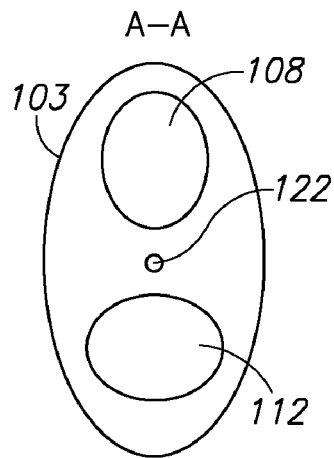
Figure 1E:
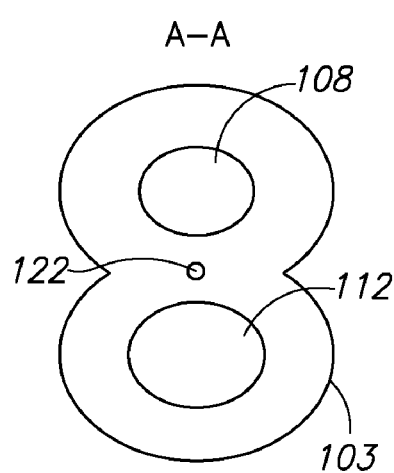
Figure 1F:
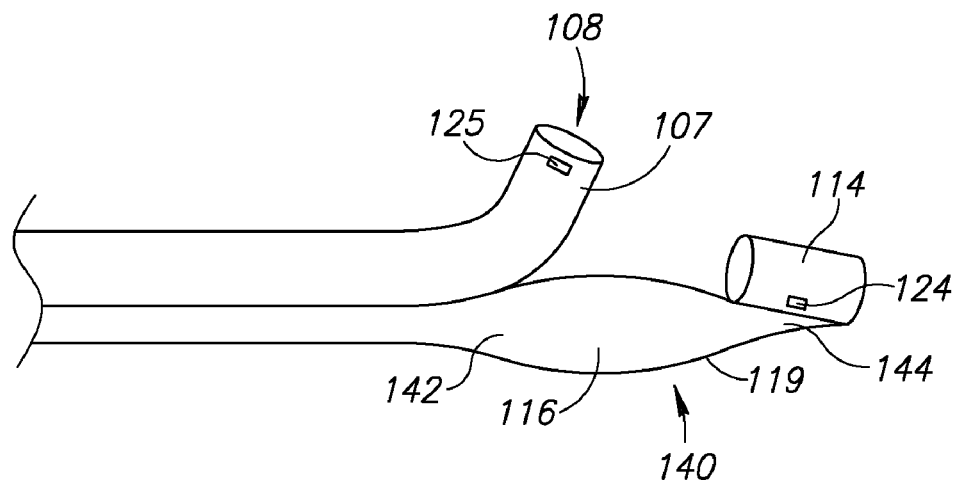
FIGS. 1F and 1G are illustrations of a distal portion of the device of FIGS. 1A and 1B in accordance with additional embodiments of the present invention.
Figure 1G:
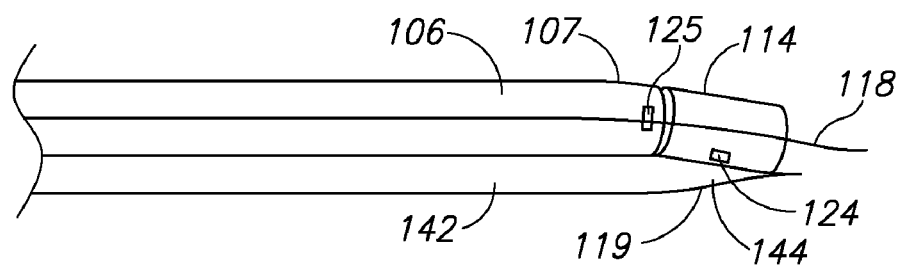

Reference is now made to FIG. 1C, which is a cross-section illustration of section A-A, showing access lumen 108 and inflation lumen 112. Inflation lumen 112 may be smaller than access lumen 108, and may assume various shapes and configurations, provided that there is sufficient area for introduction of an inflation fluid. The cross-sectional shape of shaft 103 may be approximately circular, as shown in FIG. 1C, elliptical, as shown in FIG. 1D, may assume a figure-eight configuration, as shown in FIG. 1E, or may be any other suitable shape or configuration. In some embodiments, a core wire 122 is positioned through device 100 to provide stiffness and enhance pushability and trackability. Additionally, stiffness of proximal end 102 of shaft 103 may be provided by braiding or by other methods known in the art. Stiffness improves overall pushability and torqueability.

Reference is now made to FIGS. 2A and 2B, which are schematic illustrations of a device 200 in accordance with alternative embodiments of the present invention, shown in a deployed state and in a pre-deployed state, respectively. Device 200 includes a shaft 203 having a proximal end 202 and a distal end 204. Device 200 includes an access element 206 for accessing an area of an aneurysm, and an occlusion element 210, for providing occlusion means to the ostium of the aneurysm. Distal end 204 of shaft 203 includes an access element distal portion 207 and an occlusion element distal portion 240, wherein occlusion element distal portion 240 includes a balloon 216 having a balloon proximal end 242 and a balloon distal end 244. In the embodiment shown in FIGS. 2A and 2B, access element 206 is an elongated element extending from proximal end 202 of shaft 203 to distal end 204 of shaft 203, and includes an access lumen 208 therethrough. Proximal end 202 of shaft 203 includes an access hub 217 for introduction of a material or object through access lumen 208. Distal portion 207 of access element 206 extends distally past balloon proximal end 242 and is comprised of an elastomeric or polymeric material such as a urethane, silicone rubber, latex, nylon, any copolymers thereof, or any other suitable material. Alternatively, distal portion 207 of access element 206 includes a spring-element that provides pre-shaping. A radiopaque access marker 225 is positioned on distal portion 207 of access element 206. Occlusion element 210 is also an elongated element positioned coaxial to access element 206 and extending from proximal end 202 of shaft 203 to distal end 204 of shaft 203. Occlusion element 210 has a balloon 216 at a distal end thereof. Balloon 216 is shown in an inflated state in FIG. 2A and in a deflated state in FIG. 2B. An inflation lumen 212 provides fluid communication between an inflation port 215 at proximal end 202 of shaft 203 and balloon 216. Distal portion 207 of access element 206 protrudes through a portion of balloon 216. Additional radiopaque markers 224 are positioned along occlusion element 210 and/or shaft 203.

A distal connecting element 214 is positioned at a distal end of device 200, and may be attached to balloon 216. Alternatively, distal connecting element 214 may be attached to a distal tip, distal to balloon 216. As shown in FIG. 2A, distal portion 207 of access element 206 is pre-shaped at an angle to a longitudinal axis 246 of device 200, wherein longitudinal axis 246 is defined by an imaginary line connecting distal end 204 and proximal end 202 of shaft 203. The angle can be in a range of 0 to 90 degrees, and in most cases is in a range of 20-70 degrees.

As shown in FIG. 2B, pre-shaped access element 206 can be forcibly aligned with longitudinal axis 246 of device 200 by placing a guidewire 218 therethrough and further positioning guidewire 218 through distal connecting element 214. This relatively straight configuration results in a reduced profile which is suitable for introduction and advancement through blood vessels. In one embodiment, access element 206 acts as a microcatheter for providing treatment coils. In an alternative embodiment, access element 206 acts as a conduit for a separate microcatheter placed therein.

Reference is now made to FIG. 2C, which is a cross-section illustration of section B-B, showing access lumen 208 and inflation lumen 212 in a position which is coaxial to access lumen 208. The cross-sectional shape of shaft 203 may be approximately circular, as shown in FIG. 2C, or may be elliptical, may assume a figure-eight configuration, or may be any other suitable shape or configuration. In some embodiments, a core wire 222 is positioned through device 200 and alongside access element 206 to provide stiffness. Additionally, stiffness of proximal end 202 of shaft 203 may be provided by braiding or by other methods known in the art. Stiffness improves overall pushability and torqueability.

Figure 3A:
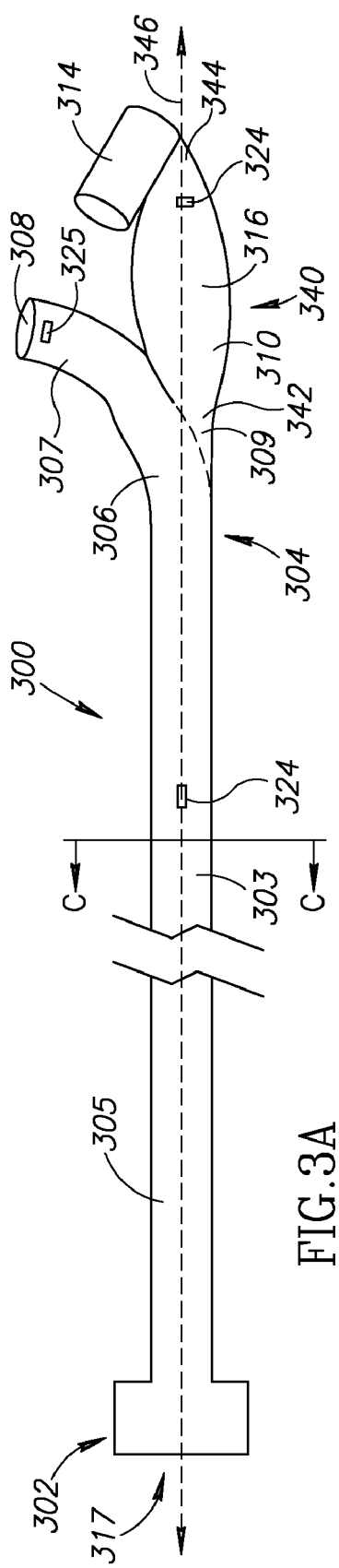
FIGS. 3A and 3B are schematic illustrations of a device in accordance with further embodiments of the present invention, shown in a deployed state and a pre-deployed state, respectively.
Figure 3B:
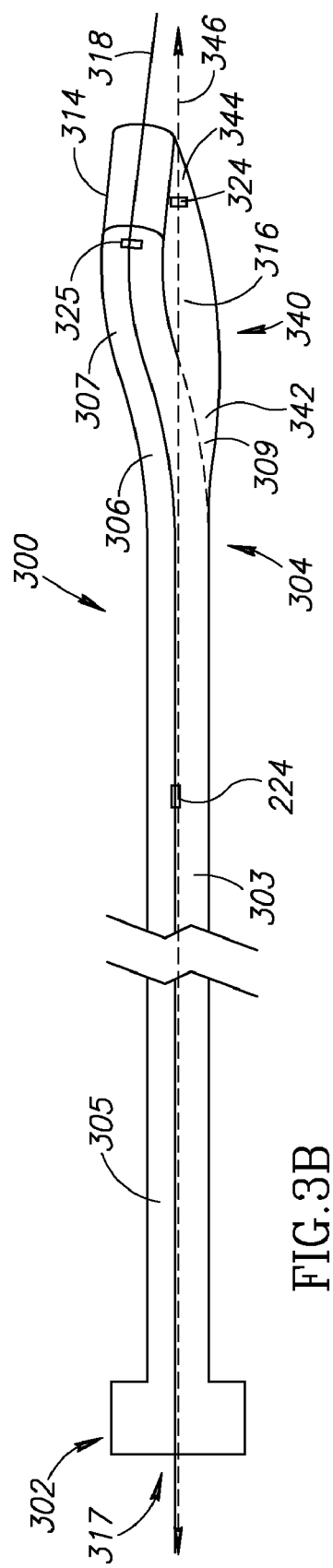

Reference is now made to FIGS. 3A and 3B, which are schematic illustrations of a device 300 in accordance with embodiments of the present invention, shown in a deployed state and in a pre-deployed state, respectively. Device 300 includes a shaft 303 having a proximal end 302 and a distal end 304. Device 300 includes an access element 306 for accessing an area of an aneurysm, and an occlusion element 310, for providing occlusion means to the ostium of the aneurysm. Distal end 304 of device 300 includes an access element distal portion 307 and an occlusion element distal portion 340, wherein occlusion element distal portion 340 includes a balloon 316 having a balloon proximal end 342 and a balloon distal end 344. In the embodiment shown in FIGS. 3A and 3B, access element 306 is an elongated element extending distally past balloon proximal end 342, and includes an access lumen 308 therethrough. Access element 306 is comprised of an elastomeric or polymeric material such as a urethane, silicone rubber, latex, nylon, any copolymers thereof, or any other suitable material. Alternatively, distal portion 207 of access element 206 includes a spring-element that provides pre-shaping. A radiopaque access marker 325 is positioned on distal portion 307 of access element 306. Proximal end 302 of shaft 303 has a larger diameter than distal portion 304 of shaft 303 and than access element 306. Occlusion element 310 is a balloon 316 positioned at distal end 304 of shaft 303. Both access lumen 308 and balloon 316 are in communication with shaft 303, and may be accessed via a shared hub 317. Balloon 316 is shown in an inflated state in FIG. 3A and in a deflated state in FIG. 3B. In one embodiment, a divider 309 partially separates balloon 316 from shaft 303, allowing fluid flow but not allowing transfer of denser materials. This configuration allows for a microcatheter having an outer diameter which is approximately equal to an inner diameter of access element 306 to be introduced through access lumen 308, effectively sealing access element 306. Once the microcatheter is in place in the aneurysm, inflation fluid can be introduced through shaft 303, and will flow directly into balloon 316. Additional radiopaque markers 324 are positioned along occlusion element 310 and/or shaft 303.

A distal connecting element 314 is positioned at a distal end of device 300, and may be attached to balloon 316. Alternatively, distal connecting element 314 may be attached to a distal tip, distal to balloon 316. As shown in FIG. 3A, access element 306 is pre-shaped at an angle to a longitudinal axis 346 of device 300, wherein longitudinal axis 346 is defined by an imaginary line connecting distal end 304 and proximal end 302 of shaft 303. The angle can be in a range of 0 to 90 degrees, and in most cases is in a range of 20-70 degrees.

As shown in FIG. 3B, pre-shaped access element 306 can be forcibly aligned with longitudinal axis 346 of device 300 by placing a guidewire 318 therethrough and further positioning guidewire 318 through distal connecting element 314. This relatively straight configuration results in a reduced profile which is suitable for introduction and advancement through blood vessels. In one embodiment, access element 306 acts as a microcatheter for providing treatment coils. In an alternative embodiment, access element 306 acts as a conduit for a separate microcatheter placed therein.

Figure 3C:
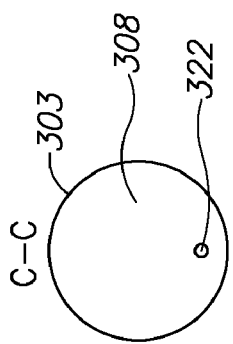
FIG. 3C is a cross-section illustration of the device of FIGS. 3A and 3B, showing an access lumen, a shaft and a core wire.

Reference is now made to FIG. 3C, which is a cross-section illustration of section C-C showing access lumen 308 and shaft 303. The cross-sectional shape of shaft 303 may be approximately circular, as shown in FIG. 3C, or may be elliptical, may assume a figure-eight configuration, or may be any other suitable shape or configuration. In some embodiments, a core wire 322 is positioned through device 300 to provide stiffness. Additionally, stiffness of proximal end 302 of shaft 303 may be provided by braiding or by other methods known in the art. Stiffness improves overall pushability and torqueability.

Figure 4A:
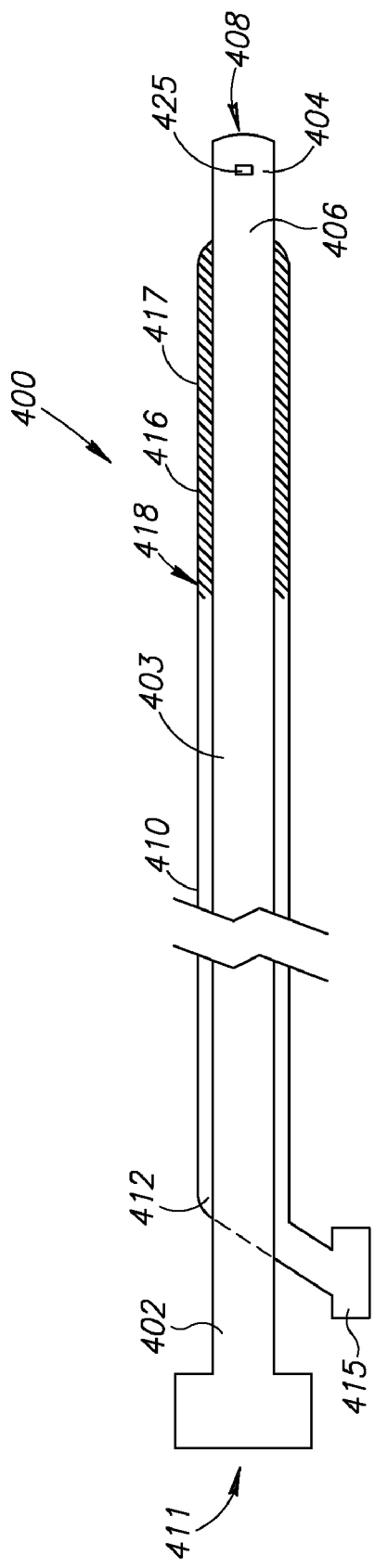
FIGS. 4A and 4B are schematic illustrations of a device in accordance with further embodiments of the present invention, shown in a pre-deployed state and in a deployed state, respectively.
Figure 4B:
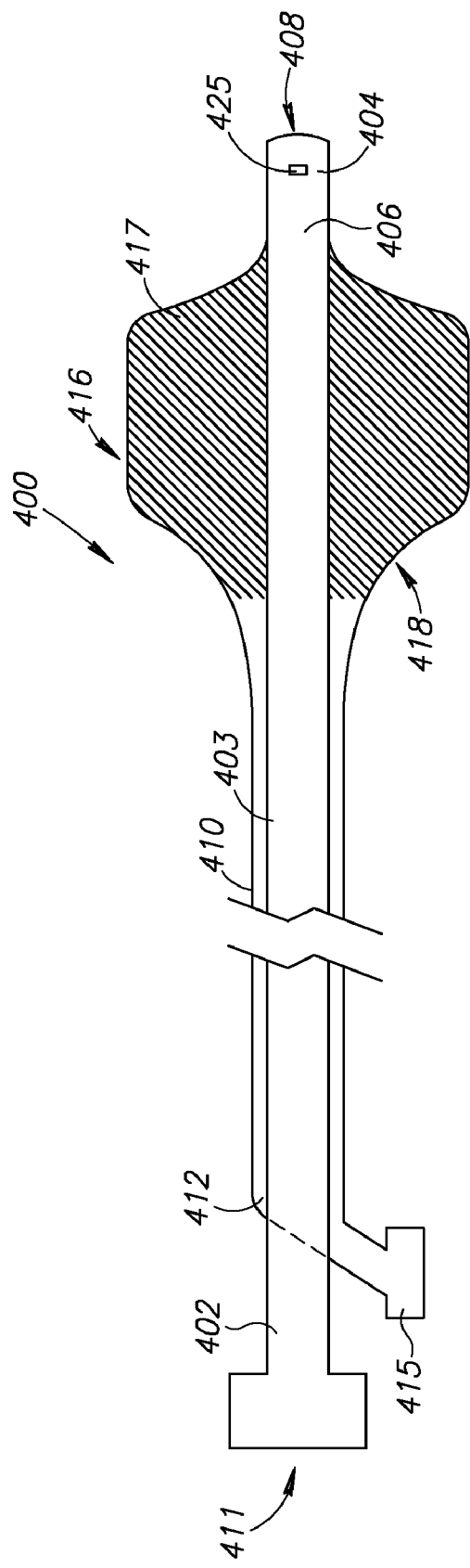

Reference is now made to FIGS. 4A and 4B, which are schematic illustrations of a device 400 in accordance with embodiments of the present invention, shown in a pre-deployed state and in a deployed state, respectively. Device 400 includes a shaft 403 having a proximal end 402 and a distal end 404. Device 400 includes an access element 406 for accessing an area of an aneurysm, and an occlusion element 410, for providing occlusion means to the ostium of the aneurysm. In the embodiment shown in FIGS. 4A and 4B, access element 406 is an elongated element extending from an access port 411 along a body of device 400 to distal end 404 of shaft 403, and includes an access lumen 408 therethrough. A radiopaque access marker 425 is positioned on a distal portion of access element 406. Occlusion element 410 is an elongated element extending from proximal end 402 of shaft 403 to a location proximal to distal end 404 of shaft 403. Occlusion element 410 includes a balloon 416 having a distal portion 417 and a proximal portion 418. Distal portion 417 has a different compliance than proximal portion 418. The difference in compliance may be provided by the use of different materials for distal portion 417 and proximal portion 418. Alternatively, the same material may be used, but with different durometers or thicknesses. Any other known method of providing an object with two different compliances may be used. In a preferred embodiment, distal portion 417 has a lower compliance than proximal portion 418. In other embodiments, distal portion 417 has a higher compliance than proximal portion 418. Balloon 416 is shown in a deflated state in FIG. 4A and in an inflated state in FIG. 4B. An inflation lumen 412 provides fluid communication between an inflation port 415 at proximal end 402 of shaft 403 and balloon 416.

While generally not recommended for endovascular aneurysm treatment, there may be some cases where the use of a stent may be beneficial. It should be readily apparent that a stent may be positioned at a distal end of any of the devices described above, and that balloon 116, 216 or 316 may be used to deploy the stent.

In some embodiments, a fixed wire is added to the distal end of balloon 116, 216, 316 or to a distal tip of the device. This wire can aid in rotation of the device and can enhance torqueability.

Reference is now made to FIGS. 5A, 5B, 5C and 5D, which are schematic illustrations of a device 500 in accordance with embodiments of the present invention. In a first embodiment, shown in FIG. 5A in a deployed state and in FIG. 5B in a pre-deployed state, device 500 includes a shaft 503 having a proximal end 502 and a distal portion 504. Device 500 includes an access element 506 for accessing an area of an aneurysm, and an occlusion element 510, for providing occlusion means to the aneurysm. Access element 506 is an elongated element extending from proximal end 502 of shaft 503 to distal portion 504 of shaft 503, and includes an access lumen 508 therethrough. A distal portion 507 of access element 506 is comprised of a soft elastomeric or polymeric material such as a urethane, silicone rubber, latex, nylon, any copolymers thereof, or any other suitable material. Alternatively, distal portion 507 of access element 506 includes a spring-element that provides pre-shaping.

A radiopaque access marker 525 is positioned on distal portion 507 of access element 506. Occlusion element 510 is also an elongated element positioned alongside and attached to access element 506, and extending from proximal end 502 of shaft 503 to distal portion 504 of shaft 503. Occlusion element 510 includes an occlusion lumen 512 for introduction of occlusion material, such as a coil, therethrough. A distal portion 513 of occlusion element 510 is comprised of a soft elastomeric or polymeric material such as a urethane, silicone rubber, latex, nylon, any copolymers thereof, or any other suitable material. Alternatively, distal portion 513 of occlusion element 510 includes a spring-element that provides pre-shaping. Additional radiopaque markers 524 may be positioned along occlusion element 510. In one embodiment, shaft 503 is a dual lumen shaft having an access lumen 508 and an occlusion lumen 512.

Distal portions 507 and 513 are pre-shaped at an angle to a longitudinal axis of device 500, wherein the longitudinal axis is defined by an imaginary line connecting distal portion 504 and proximal end 502 of shaft 503. The angle can be in a range of 0 to 90 degrees, and in most cases is in a range of 20-70 degrees. Proximal end 502 of shaft 503 includes an access hub 517 for introduction of a material or object through access lumen 508, and an occlusion hub 519 for introduction of a material or object through occlusion lumen 512.

Figure 5A:
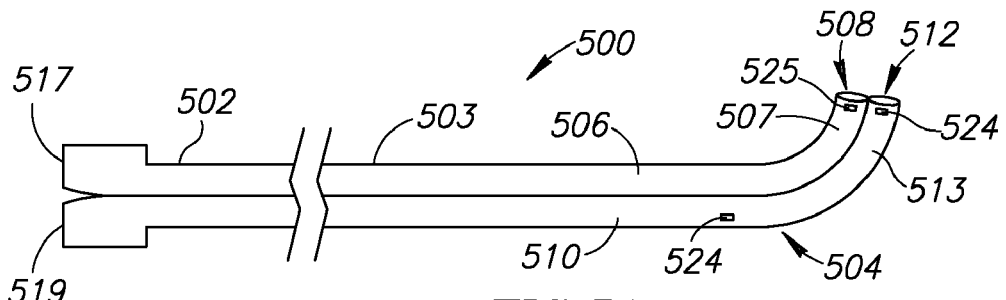
FIGS. 5A-5D are schematic illustrations of a device in accordance with yet further embodiments of the present invention, shown in deployed states in FIGS. 5A and 5C and in pre-deployed states in FIGS. 5B and 5D.
Figure 5B:
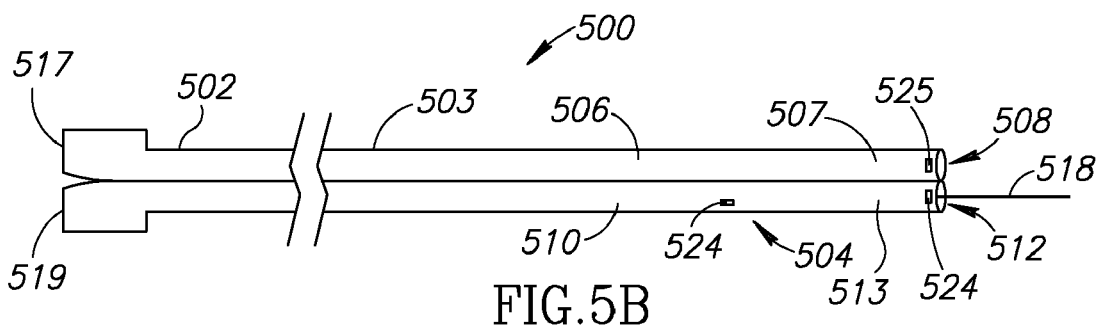

Device 500 is shown in a pre-deployed position in FIG. 5B, wherein a guidewire 518 positioned through occlusion lumen 512 forcibly aligns distal portions 507 and 513 with the longitudinal axis of device 500. Alternatively, guidewire 518 may be positioned through access lumen 508. This relatively straight configuration results in a reduced profile which is suitable for introduction and advancement through blood vessels. Upon removal of guidewire 518, distal ends 507 and 513 assume their pre-shaped configuration.

Figure 5C:
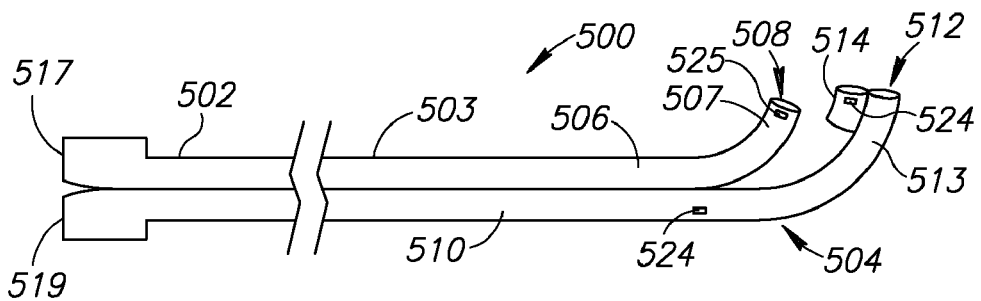
Figure 5D:
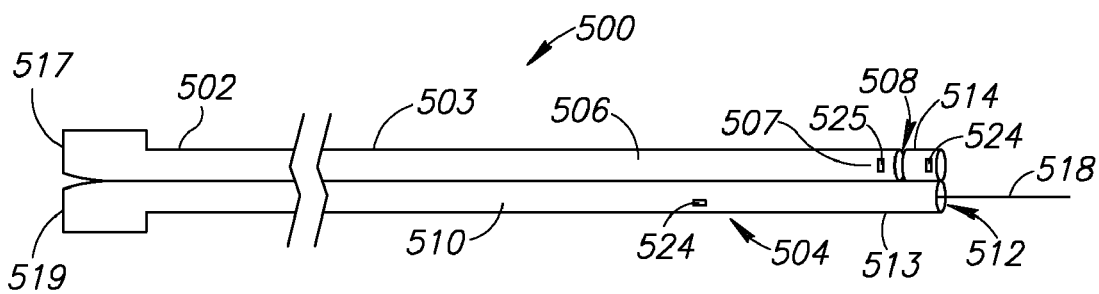

In an alternative embodiment, shown in FIGS. 5C and 5D, a distal connecting element 514 is positioned at distal end of occlusion element 510. In this embodiment, an additional radiopaque marker 524 may be positioned on distal connecting element 514. In this embodiment, pre-shaped access element 506 and pre-shaped occlusion element 510 can be forcibly aligned with the longitudinal axis of device 500 by placing a guidewire 518 through access lumen 508 and further positioning guidewire 518 through distal connecting element 514.

Figure 6A:
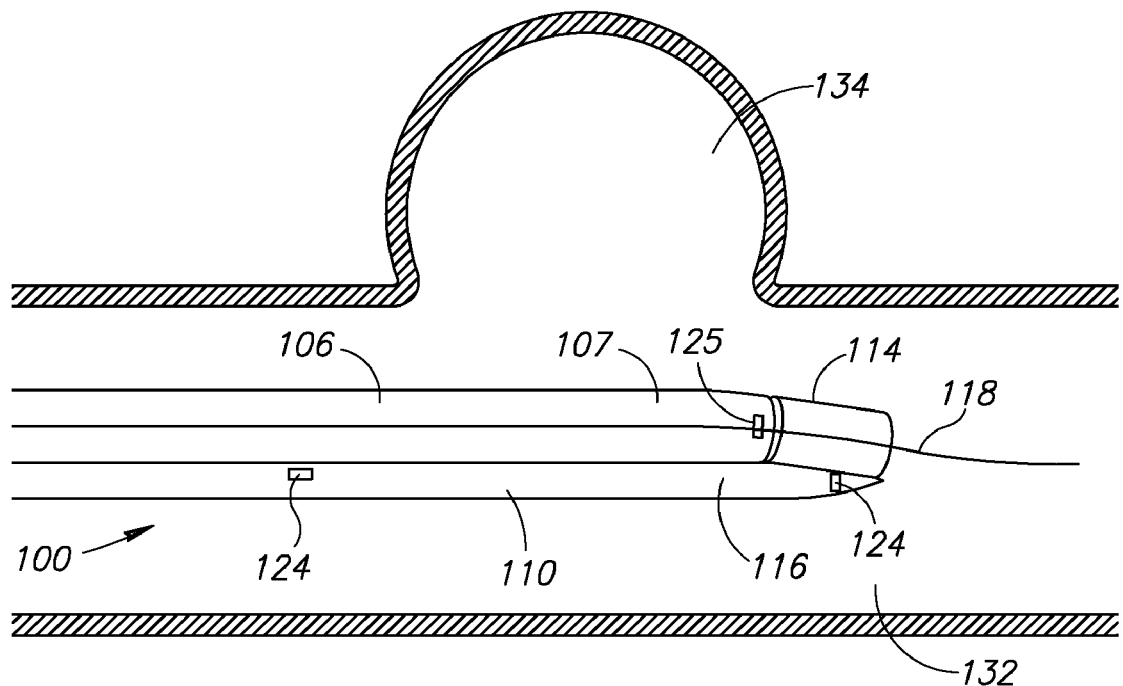
FIGS. 6A-6D are schematic illustrations of the steps of a method of using the devices of FIGS. 1A-1G or FIGS. 2A-2C, in accordance with embodiments of the present invention.
Figure 6B:
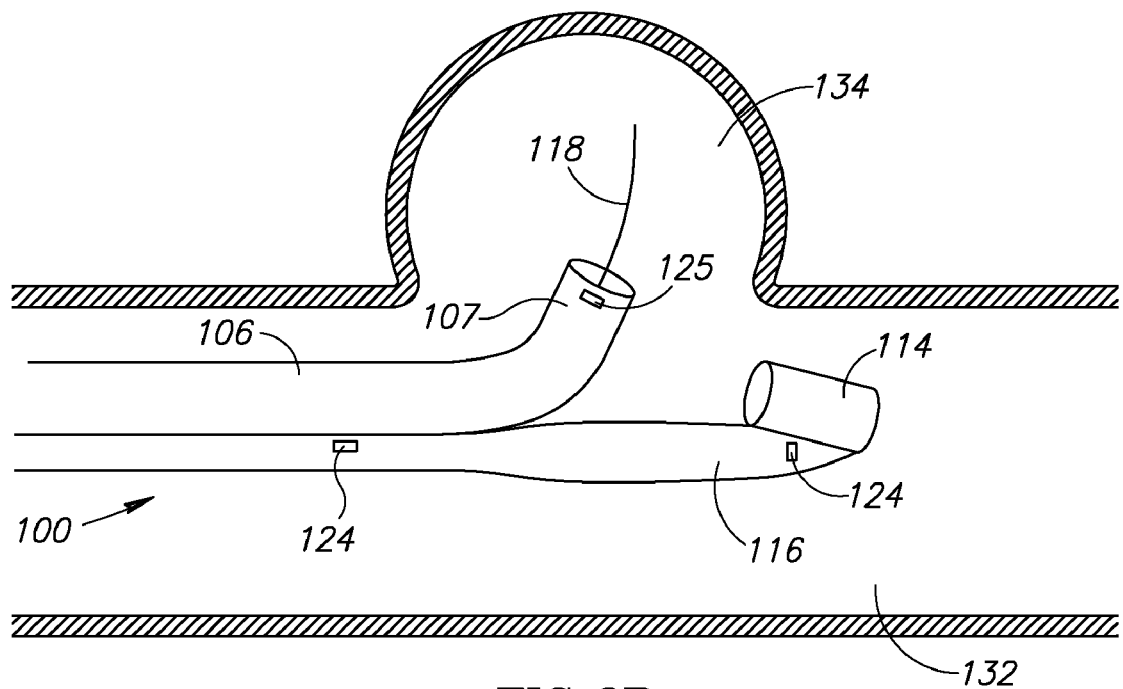
Figure 6C:
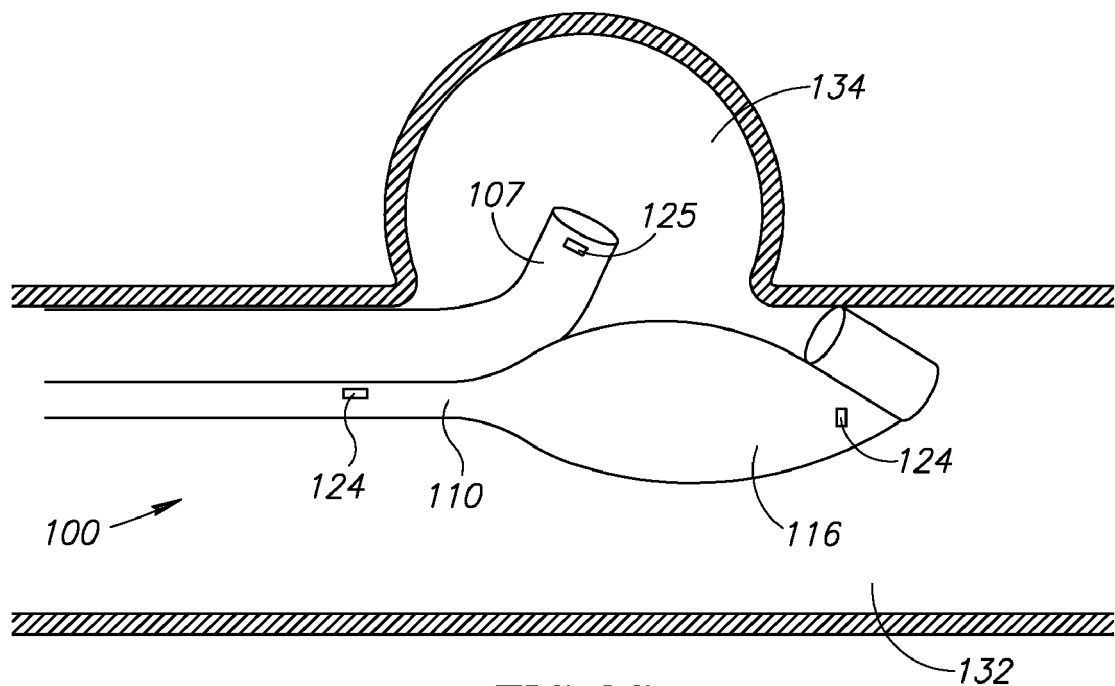
Figure 6D:
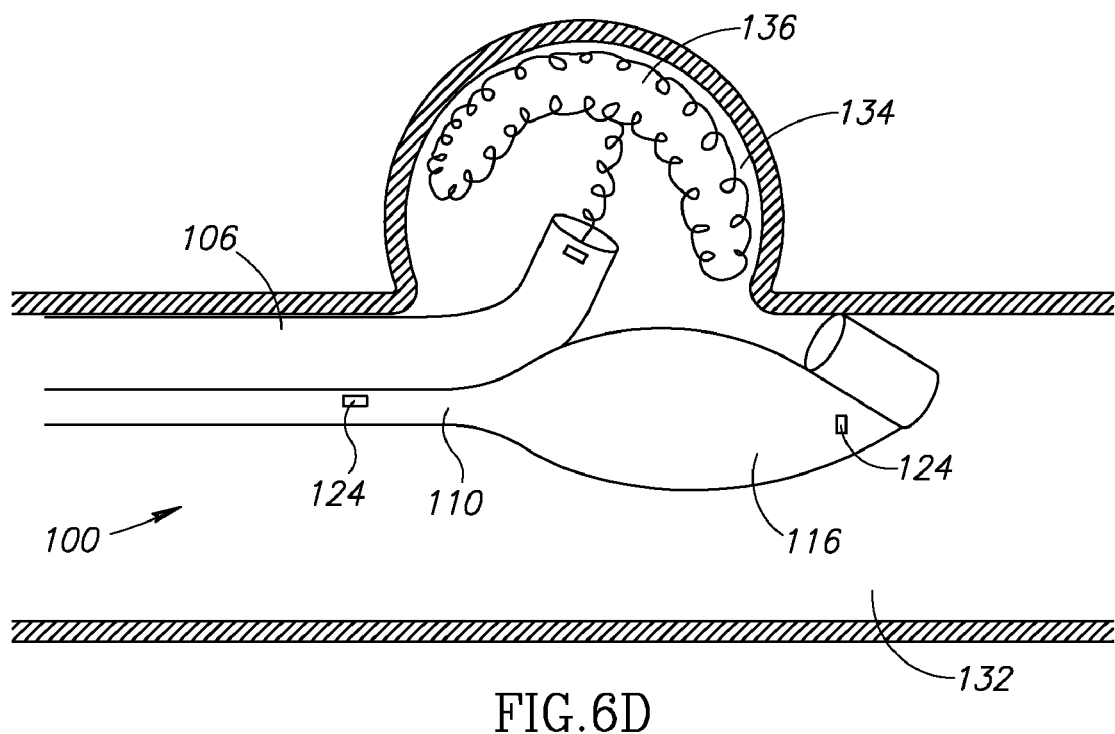

Reference is now made to FIGS. 6A-6D, which are schematic illustrations of the steps of a method of using device 100 to treat an aneurysm. Although the figures are shown and described with respect to device 100, the method for using device 200 may be the same as for device 100. As shown in FIG. 6A, device 100 is introduced over a guidewire 118 into a main vessel 132 to an area of an aneurysm 134. Device 100 is in its unexpanded state, with distal portion 107 of access element 106 held in an aligned position with device 100 via guidewire 118 placed through access element 106 and distal connecting element 114. As shown in FIG. 6B, guidewire 118 is retracted proximally, releasing guidewire 118 from distal connecting element 114, and causing distal portion 107 of access element 106 to assume its pre-shaped configuration. Distal portion 107 of access element 106 is positioned within aneurysm 134. Markers 124 and 125 are used for positioning, as will be described in further detail hereinbelow. As shown in FIG. 6C, access element 106 is positioned within aneurysm 134, and balloon 116 is expanded—blocking the neck or ostium of aneurysm 134. As shown in FIG. 6D, a coil 136 is then introduced through access lumen 108 and into aneurysm 134, in accordance with methods known in the art. Alternatively, a microcatheter is then introduced through access lumen 108, and coil 136 is delivered through the microcatheter. Balloon 116 can be inflated and deflated several times during the procedure so as to alternate between allowing normal blood passage through main vessel 132, and keeping the ostium of aneurysm 134 blocked until coil 136 is set. Once coil 136 is set, balloon 116 is deflated, and device 100 is removed from the vessel.

Figure 7A:
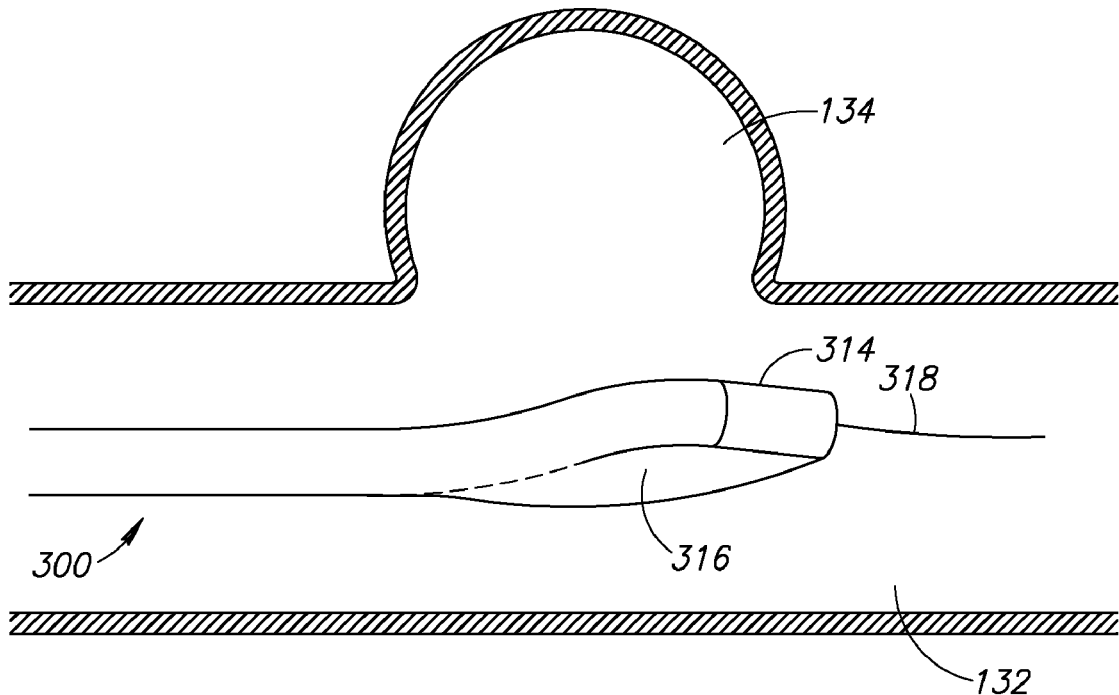
FIGS. 7A-7D are schematic illustrations of the steps of a method of using the devices of FIGS. 3A-3C, in accordance with embodiments of the present invention.
Figure 7B:
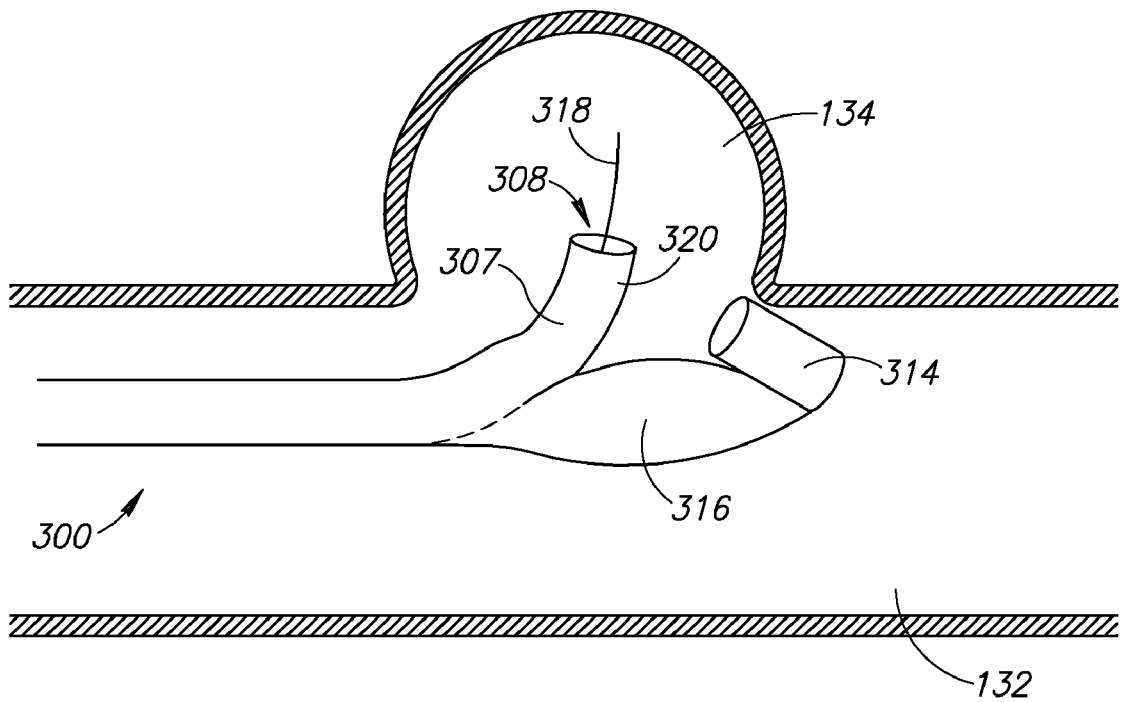
Figure 7C:
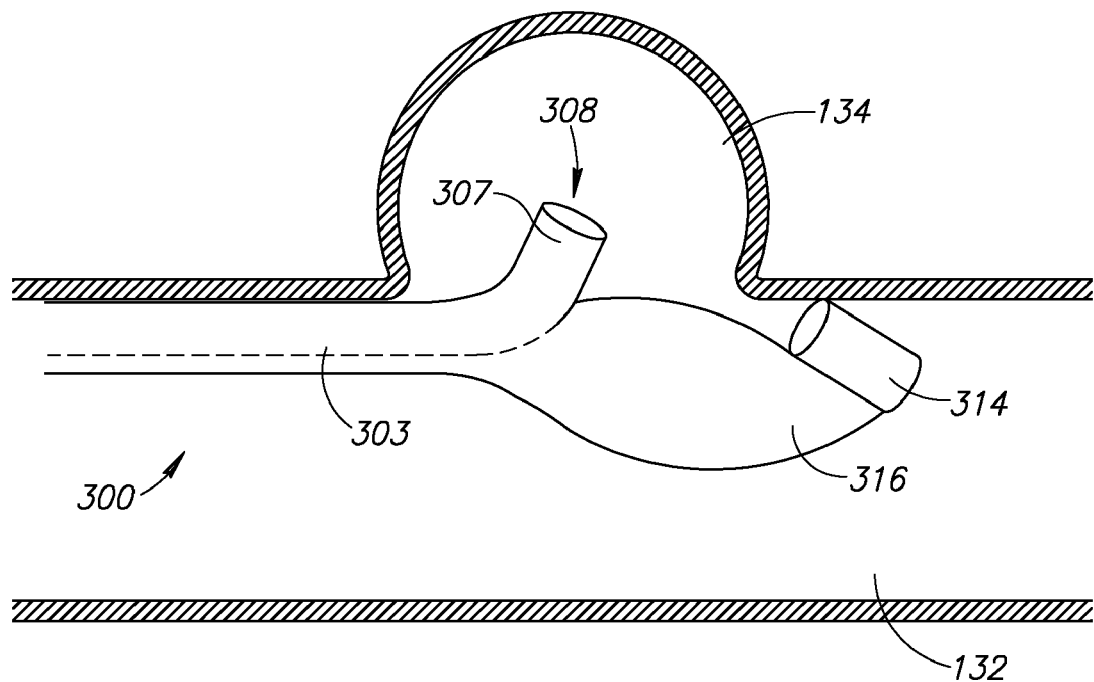
Figure 7D:
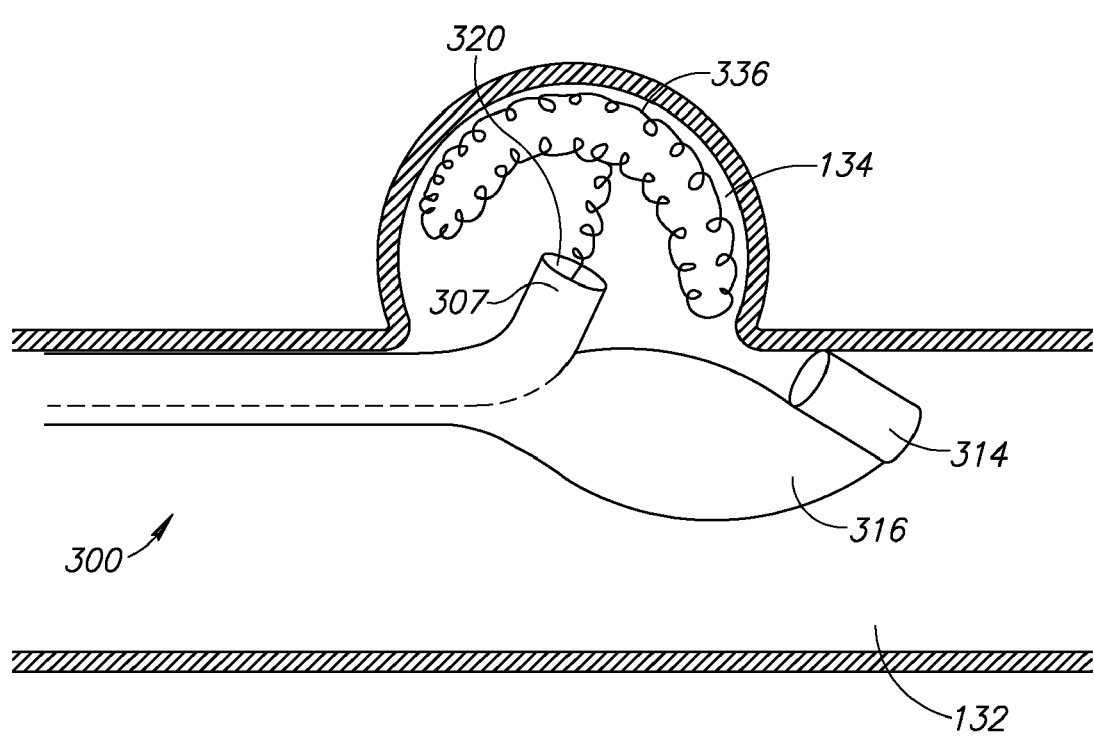

Reference is now made to FIGS. 7A-7D, which are schematic illustrations of the steps of a method of using device 300 to treat an aneurysm. As shown in FIG. 7A, device 300 is introduced over a guidewire 318 into a main vessel 132 to an area of an aneurysm 134. Device 300 is in its unexpanded state, with access element 306 held in an aligned position with device 300 via guidewire 318 placed through access element 306 and distal connecting element 314. As shown in FIG. 7B, guidewire 318 is retracted proximally, releasing guidewire 318 from distal connecting element 314, and causing distal portion 307 of access element 306 to assume its pre-shaped configuration. Distal portion 307 of access element 306 is positioned within aneurysm 134. Markers are used for positioning, as will be described in further detail hereinbelow. As shown in FIG. 7C, distal portion 307 of access element 306 is positioned within aneurysm 134. Microcatheter 320 is then positioned in access lumen 308. Microcatheter 320 effectively seals access element 306, allowing for inflation fluid to reach balloon 316. Balloon 316 is then expanded, blocking the neck or ostium of aneurysm 134. As shown in FIG. 7D, a coil 336 is then introduced through microcatheter 320 and into aneurysm 134, in accordance with methods known in the art. Balloon 316 can be inflated and deflated several times during the procedure so as to alternate between allowing normal blood passage through main vessel 132, and keeping the ostium of aneurysm 134 blocked until coil 336 is set. Once coil 336 is set, balloon 316 is deflated, and device 300 is removed from the vessel.

Figure 8A:
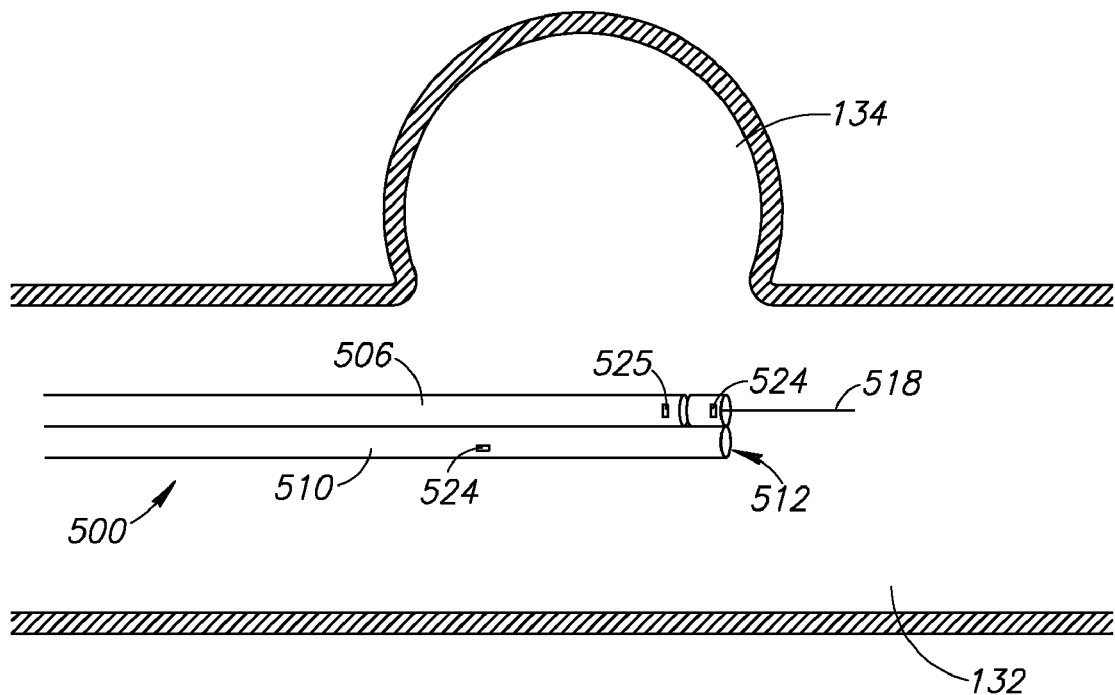
FIGS. 8A-8D are schematic illustrations of the steps of a method of using the devices of FIGS. 5A-5D, in accordance with embodiments of the present invention.
Figure 8B:
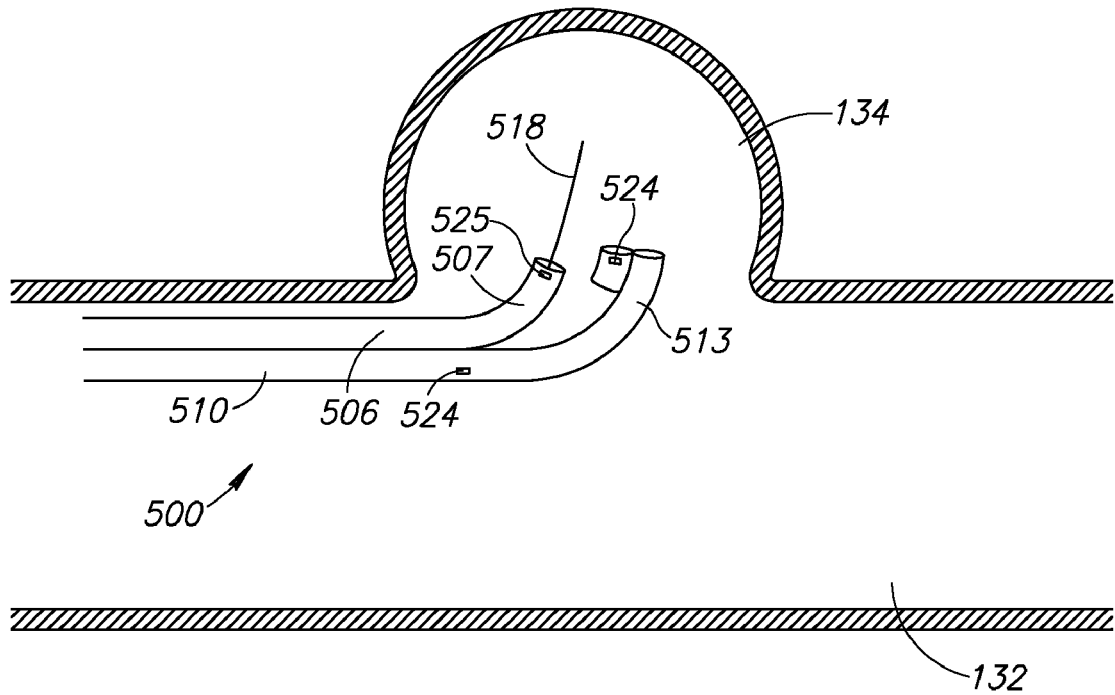
Figure 8C:
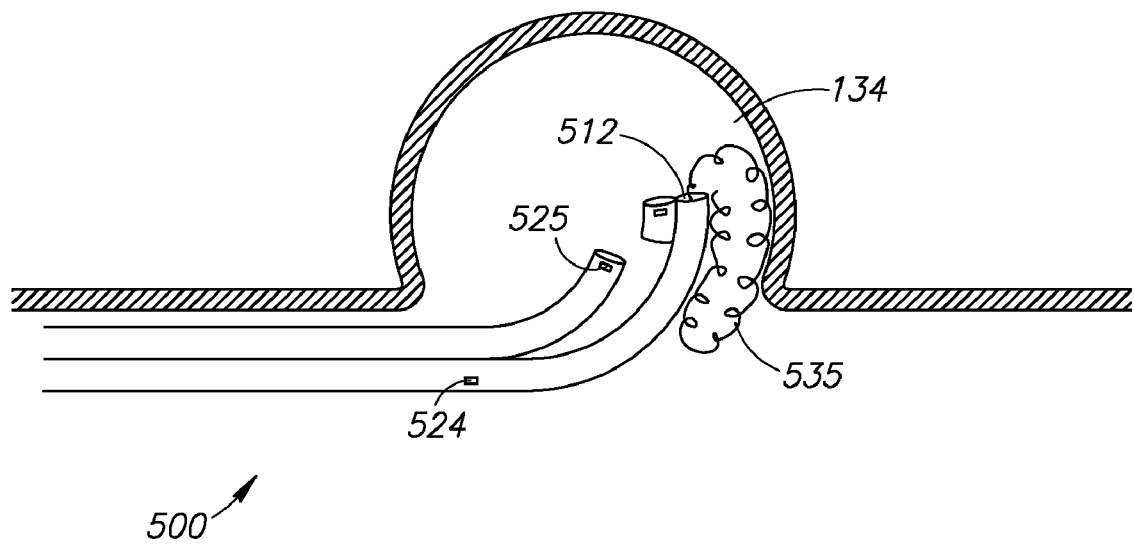
Figure 8D:
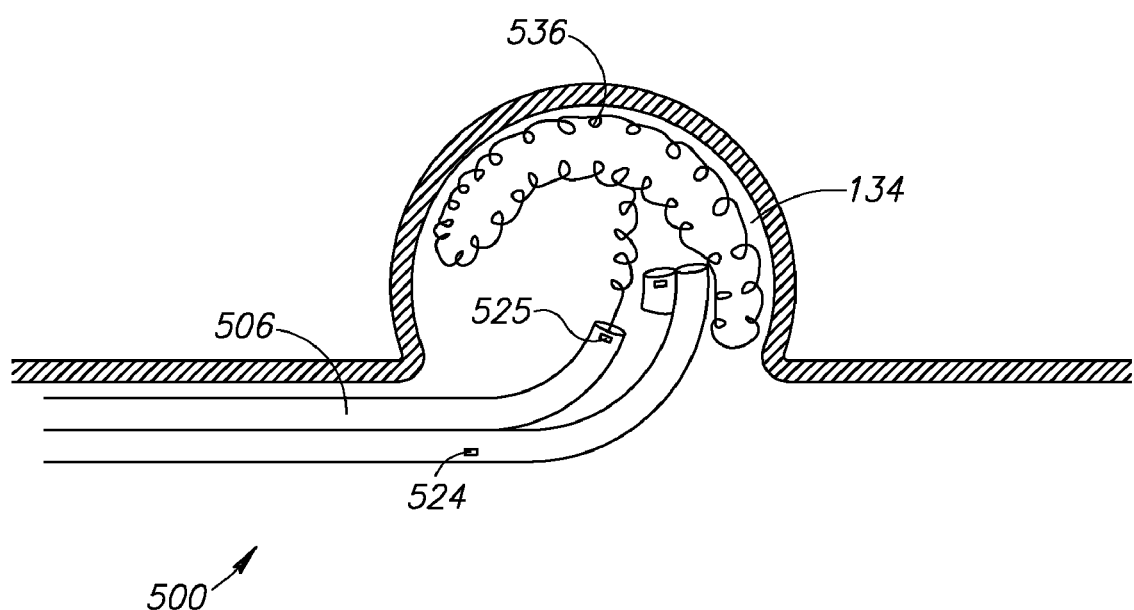

Reference is now made to FIGS. 8A-8D, which are schematic illustrations of the steps of a method of using device 500 to treat an aneurysm. Although the figures are shown and described with respect to one embodiment of device 500, the method for using other embodiments of device 500 may be the same as the method depicted in FIGS. 8A-8D. As shown in FIG. 8A, device 500 is introduced over a guidewire 518 into a main vessel 132 to an area of an aneurysm 134. Device 500 is in its undeployed state, with access element 506 and occlusion element 510 held in an aligned position via guidewire 518 placed through access element 506 and distal connecting element 514. As shown in FIG. 8B, guidewire 518 is retracted proximally, releasing guidewire 518 from distal connecting element 514, and causing distal portion 507 of access element 506 and distal portion 513 of occlusion element 510 to assume their pre-shaped configurations. Distal portion 507 of access element 506 and distal portion 513 of occlusion element 510 are positioned within aneurysm 134. Markers 524 and 525 are used for positioning, as will be described in further detail hereinbelow. As shown in FIG. 8C, a blocking coil 535 is introduced through occlusion lumen 512 and into aneurysm 134—blocking the neck or ostium of aneurysm 134. As shown in FIG. 8D, one or more coils 136 are then introduced through access lumen 508 and into aneurysm 134, in accordance with methods known in the art. After coils 136 are delivered into aneurysm 134 and detached, and satisfactory filling of the aneurysm is confirmed, blocking coil 535 is detached. Detachment of coils 136 and blocking coil 535 is achieved in accordance with methods known in the art. Alternatively, a microcatheter is introduced through occlusion lumen 512 to deliver blocking coil 535, and a microcatheter is introduced through access lumen 108 to deliver coils 136. This method alleviates the long occlusion time or potential vessel damage sometimes associated with the use of balloons for occlusion.

Reference is now made to FIGS. 9A-9C, which are schematic illustrations of a method of using device 100 to treat an aneurysm at a Y-bifurcation, such as a vertebrobasilar junction. In this type of vessel, an aneurysm 234 may be positioned just opposite a main vessel 232, and must be accessed head-on rather than from an angle. Although the method is shown for device 100, it should be readily apparent that any of the devices in accordance with the various embodiments may be similarly used. As shown in FIG. 9A, device 100 is introduced over a guidewire 118 through main vessel 232. As shown in FIG. 9B, access element 106 is positioned in aneurysm 134. Balloon 116 is then inflated, as shown in FIG. 9C. In some instances, balloon 116 is compliant enough to block the ostium on its own. In other instances, it may be useful to introduce a second device with balloon 116 positioned over the remainder of ostium 134. Once the ostium is blocked, coil 136 is introduced into aneurysm 134, as described above with respect to FIGS. 6A-6D, 7A-7D and 8A-8D.

Reference is now made to FIGS. 10A-10C, which are schematic illustrations of a method of using device 400 to treat an aneurysm at a Y-bifurcation, such as a vertebrobasilar junction. In this type of vessel, an aneurysm 234 may be positioned just opposite a main vessel 232, and must be accessed head-on rather than from an angle. As shown in FIG. 10A, device 400 is introduced over a guidewire 419 through main vessel 232. As shown in FIG. 10B, access element 406 is positioned in aneurysm 134, and balloon 416 is inflated. The high compliance of proximal portion 418 causes proximal portion 417 to be inflated over a wide area, causing the ostium to be substantially blocked. The low compliance of distal portion 417 prevents balloon 416 from expanding into aneurysm 234. Once the ostium is blocked, coil 136 is introduced into aneurysm 234, as described above with respect to FIGS. 6A-6D, 7A-7D, 8A-8D, and 9A-9D.

Figure 11A:
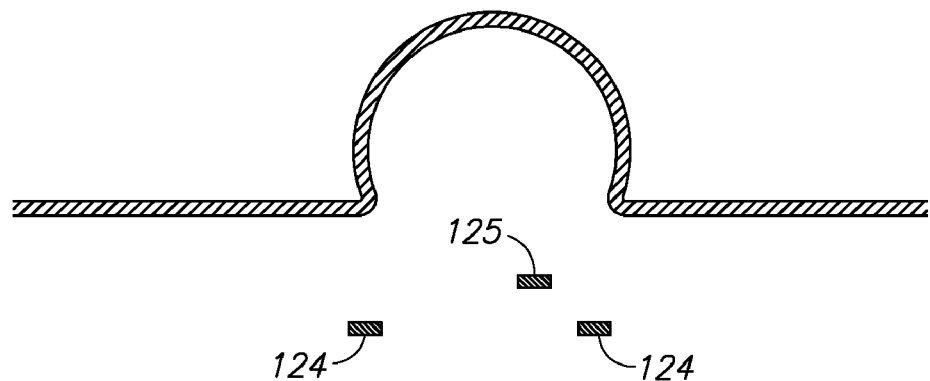
FIGS. 11A-11C are schematic illustrations of views of marker positions in accordance with several different positions of the devices of the present invention.
Figure 11B:
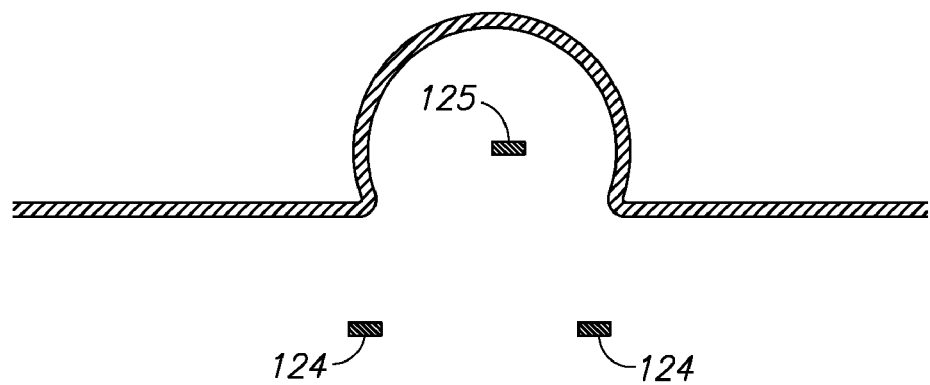
Figure 11C:
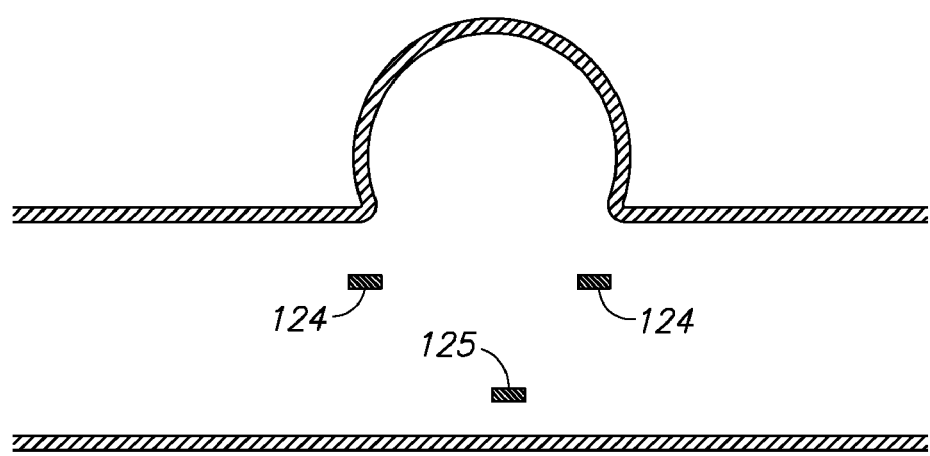

Reference is now made to FIGS. 11A, 11B and 11C, which are illustrations of several views of marker positioning. Marker 125, positioned on distal portion 107 of access element 106, and markers 124, positioned along the longitudinal axis of device 100, together provide an indication of positioning and location. It should be readily apparent that similar configurations are provided in the alternative embodiments of device 200, 300, 400, and 500. In a first view, shown in FIG. 11A, markers 124 form a relatively straight line, while marker 125 is slightly off the line formed by markers 124. This indicates translational positioning of device 100 prior to deployment. When the distal portion 107 of access element 106 of device 100 is released, it assumes its pre-shaped configuration, and marker 125 moves to a position which is further off the line formed by markers 124, as shown in FIG. 11B. If positioning is inaccurate, marker 125 appears at a side opposite the aneurysm, as shown in FIG. 11C. Thus, if a user views the view shown in FIG. 11C or a similar view, the user can then rotate device 100 until it is in the correct position as indicated by the position of markers 124 and 125 as shown in FIG. 11B. This specific configuration of markers allows for proper alignment and positioning within the vessel.

In additional embodiments of the invention, access element 106, 206, 306, 406 or 506 may include multiple access lumens. Moreover, points of attachment of access element 106, 206, 306 or 506 to occlusion element 110, 210, 310 or 510, respectively, may vary. In one embodiment, the access element is attached at a midpoint of the balloon. In other embodiments, the access element is attached at a proximal end of the balloon, at a distal end of the balloon, or at any point in between.

While certain features of the invention have been illustrated and described herein, many modifications, substitutions, changes, and equivalents may occur to those of ordinary skill in the art. It is, therefore, to be understood that the appended claims are intended to cover all such modifications and changes as fall within the true spirit of the invention.

What is claimed is:

1. A device for providing a coil to an aneurysm, the device comprising:
   an access element having an access element proximal end, an access element distal end, and an access element body extending from said access element proximal end to said access element distal end, said access element body having an access lumen therethrough for providing a treatment material to a vessel said access element distal end biased to assume a pre-shaped configuration at an angle to a longitudinal axis of the device;
   an occlusion element for occluding an ostium of the aneurysm during delivery of the coil, said occlusion element comprising:
      an elongated element positioned alongside said access element, said elongated element having an elongated element proximal end, an elongated element distal end and an inflation lumen therethrough; and a balloon positioned at said elongated element distal end, said balloon inflatable via said inflation lumen;

a distal connecting element positioned distal to said access element distal end and substantially aligned with said access element; and a guidewire removably positioned through said access element and said distal connecting element such that said access element distal end is forcibly aligned with said longitudinal axis when said guidewire is positioned through said distal connecting element, and said access element distal end assumes its pre-shaped angle upon removal of said guidewire from said distal connecting element.

2. The device of claim 1, wherein said access element distal end is comprised of a soft material.

3. The device of claim 1, wherein said access element distal end includes a spring-element that provides said bias for said pre-shaped configuration.

4. The device of claim 1, further comprising a radiopaque marker on said access element distal end.

5. The device of claim 1 wherein said access element distal end extends past a proximal end of said balloon.

6. The device of claim 1, wherein said distal connecting element is attached to said occlusion element.

7. The device of claim 1, wherein said distal connecting element is attached to the device distal to said occlusion element.

8. The device of claim 1, wherein said access element and said occlusion element are positioned within a shaft, the device further comprising a core wire positioned through said shaft.

9. The device of claim 1, wherein said occlusion element comprises an elongated element positioned coaxial to said access element.

10. The device of claim 9, wherein said access element distal end protrudes through a portion of said occlusion element.

11. The device of claim 1, wherein said access element and said balloon are in fluid communication with a single lumen, wherein said fluid communication may be selectively blocked to said balloon upon introduction of an object through said access lumen.

12. The device of claim 1, wherein said balloon comprises a balloon distal portion and a balloon proximal portion, said balloon distal portion having a different compliance than said balloon proximal portion.

13. The device of claim 1, further comprising a fixed wire at a distal end of the balloon.

* * * * *